United States Patent
Fhaner et al.

(10) Patent No.: US 10,130,574 B2
(45) Date of Patent: Nov. 20, 2018

(54) NITRONE INHIBITION OF OXIDATION OF UNSATURATED FATS

(71) Applicants: Dow Global Technologies LLC, Midland, MI (US); Rohm and Haas Company, Collegeville, PA (US)

(72) Inventors: Cassie Fhaner, Freeland, MI (US); Kinjalbahen Joshi, Collegeville, PA (US); Yujing Tan, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

(21) Appl. No.: 15/558,014

(22) PCT Filed: Mar. 18, 2016

(86) PCT No.: PCT/US2016/023183
§ 371 (c)(1),
(2) Date: Sep. 13, 2017

(87) PCT Pub. No.: WO2016/154022
PCT Pub. Date: Sep. 29, 2016

(65) Prior Publication Data
US 2018/0071186 A1   Mar. 15, 2018

Related U.S. Application Data

(60) Provisional application No. 62/136,121, filed on Mar. 20, 2015.

(51) Int. Cl.
| A61Q 19/00 | (2006.01) |
| A61K 8/40 | (2006.01) |
| A61K 8/34 | (2006.01) |
| A61Q 19/10 | (2006.01) |
| A61K 8/92 | (2006.01) |
| A61K 8/36 | (2006.01) |

(52) U.S. Cl.
CPC ............. *A61K 8/40* (2013.01); *A61K 8/347* (2013.01); *A61K 8/361* (2013.01); *A61K 8/922* (2013.01); *A61Q 19/00* (2013.01); *A61Q 19/10* (2013.01); *A61K 2800/522* (2013.01)

(58) Field of Classification Search
CPC ................. A61K 8/347; A61Q 19/00
See application file for complete search history.

(56) References Cited

U.S. PATENT DOCUMENTS

| 5,176,983 A | 1/1993 | Horn et al. |
| 5,273,863 A | 12/1993 | Horn et al. |
| 5,455,272 A | 10/1995 | Janzen et al. |
| 6,002,001 A | 12/1999 | Carney et al. |
| 6,428,461 B1 | 8/2002 | Marquez et al. |
| 7,655,251 B2 | 2/2010 | Durand et al. |
| 9,452,118 B2 | 9/2016 | Dhamdhere et al. |
| 9,452,119 B2 | 9/2016 | Dhamdhere et al. |
| 9,701,625 B2 | 7/2017 | Green et al. |
| 9,730,874 B2 | 8/2017 | Green et al. |
| 9,796,667 B2 | 10/2017 | Green et al. |
| 9,828,335 B2 | 11/2017 | Green et al. |
| 2004/0241261 A1 | 12/2004 | Prous et al. |
| 2008/0096963 A1* | 4/2008 | Jean ............. A61K 31/20 514/560 |
| 2010/0168112 A1 | 7/2010 | Kelly et al. |
| 2012/0058088 A1 | 3/2012 | Sardi |
| 2014/0303255 A1 | 10/2014 | Dhamdhere et al. |
| 2017/0135941 A1 | 5/2017 | Green et al. |
| 2018/0055749 A1 | 3/2018 | Fhaner et al. |

FOREIGN PATENT DOCUMENTS

| CN | 102153498 | 8/2011 |
| DE | 10201223 | 7/2003 |
| EP | 1284133 | 2/2003 |
| EP | 1591104 | 11/2005 |
| ES | 2316312 | 4/2009 |
| IN | I377CHE2009 | 6/2012 |
| JP | 2011251914 | 12/2011 |
| WO | 199222290 | 12/1992 |
| WO | 199511227 A1 | 4/1995 |
| WO | 2002065993 | 8/2002 |
| WO | 2005041905 A2 | 5/2005 |

(Continued)

OTHER PUBLICATIONS

Diet and I (Living a healthy life; Dec. 2012, pp. 1-9).*
Wang, M. et al; Journal of Agricultural and Food Chem; 1999, vol. 47, No. 10, pp. 3974-3977.
Hung, Chi-Feng, et al; Biol Pharm. Bull; 31(5), 2009, pp. 955-962.
Fabris, S., et al; Biophysical Chemistry, 135,2008, pp. 76-83.
Fang, J-G, et al; Journal of Agricultural and Food Chemistry, vol. 56, 2008, pp. 11458-11463.
Lee, Soo-Jin, Kim, Moon-Moo; Life Sciences, vol. 88, 2011, pp. 465-472.

(Continued)

*Primary Examiner* — Samira J Jean-Louis

(74) *Attorney, Agent, or Firm* — Edward L. Brant

(57) ABSTRACT

Provided are compositions useful for inhibiting oxidation of unsaturated fats comprising an antioxidant compound of Formula I:

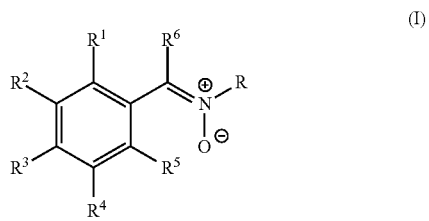

wherein R, $R^1$, $R^2$, $R^3$, $R^4$, $R^5$ and $R^6$ are as defined herein.

4 Claims, 7 Drawing Sheets

(56) References Cited

FOREIGN PATENT DOCUMENTS

| WO | 2005087214 | 9/2005 |
|---|---|---|
| WO | 2009108999 | 9/2009 |
| WO | 2011130400 | 10/2011 |
| WO | 2012150370 | 11/2012 |
| WO | 2013081778 A2 | 6/2013 |

OTHER PUBLICATIONS

Re, R. et al; Free Radical Biology & Medicine, vol. 26, No. 9/10,1999, pp. 1231-1237.
Samadi, A., et al; Bioorganic & Medicinal Chemistry, vol. 19, No. 2,2011, pp. 951-960.
Hill, R.; Internet retrieval, Spin Traps: The New Anti-Oxidants, Jan. 1, 2008.
Hill, R.; Spin Traps: The New Anti-Oxidant?; Beautymagonline [Retrieved Mar. 29, 2013], Retrieved from the Internet <URL:http://www.beautymagonline.com/beauty-articles-4/1112-spin-traps-2>, pp. 1-3.
Perricone, N., The Wrinkle Cure: The Formula for Stopping Time, Vintage/Ebury (A Division of Random); Illustrated Edition, pp. 182-186, Jul. 1, 2001.
Kliegel Etal; C-(2-Hydroxyaryl)-N-(2-Hydroxyphenylmethyl)Nitrones As Regioselective Bidentate Ligands in Boron Chelate Formation. Crystal and Molecular Structures of a Diphenylboron Complex and Its Parent Ligand, Candian Journal of Chemistry, Issue 76, vol. 7, pp. 1082-1092, 1998.
Croitour, M D. "Nitrones Are Able to Release Nitric Oxide in Aqueous Environment Under Hydroxyl Free Radical Attack", Nitric Oxide: Biology and Chemistry, vol. 25, No. 3, pp. 309-315, 2011.
Scott, G. "Mechanisms of Antioxidant Action: Rubber Bound Antioxidants Based on Nitrones-1, Non-Sulphur Vulcanizates", European Polymer Journal, vol. 14, pp. 905-912, Pergamon Press Ltd 1978.
Floyd, R. "Nitrones, Their Value as Therapeutics and Probes to Understand Aging", Mechanisms of Aging and Development 123, pp. 1021-1031, 2002.
Hensley, K. "Nitrone-Based Free Radical Traps As Neuroprotective Agents in Cerebral Schaemia and Other Pathologies", IRN 40, Chapter 13, pp. 299-317, Academic Press Limited, 1997.
Bagheri, R. "Mechanisms of Antioxidant Action: Evidence for a Regenerative Cycle During the Melt Stabilisation of Polypropylene by Galvinoxyl", Polymer Degradation and Stability, vol. 5, pp. 145-160, 1983.
Finlayson, M. "Aging With Multiple Sclerosis", J. Neurosci Nurs. vol. 36, Issue 5, pp. 1-10, 2004.
Zou, et al; Fabrication of Surface-Modified CDSE Quantum Dots by Self-Assembly of a Functionalizable Comb Polymer, Polymer International, vol. 5, Issue 60, pp. 751-757, 2011.
Kasiotis, et al; Reservatrol and Related Stilbenes: Their Anti-Aging and Anti-Angiogenic Properties; Food and Chemical Technology, vol. 61, pp. 112-120, 2013.
Burgess, C.M.; Cosmetic Dermatology, p. 19, 2005.
Velasco, et al; Electron Spin Resonance Spin Trapping for Analysis of Lipid Oxidation in Oils: Inhibiting Effect of the Spin Trap [Alpha]-Phenyl-N-Tert-Butylnitrone on Lipid Oxidation; Journal of Agricultural and Food Chemistry, vol. 53, Issue 5, pp. 1328-1336; Mar. 1 2005.

\* cited by examiner

NITRONE INHIBITION OF OXIDATION OF UNSATURATED FATS

FIELD OF THE INVENTION

This invention relates generally to compounds and compositions that are useful as antioxidants in personal care formulations. The compounds contain both nitrone and phenolic functionalities.

BACKGROUND

Personal care compositions contain a variety of additives that provide a wide array of benefits to the composition. Unsaturated fatty acids are one of such additives, and known to be important for the preservation of the skin-barrier function and water content of skin. Due to their structure, unsaturated fatty acids can enhance the fluidity of cell membranes, which lead to a more moistened and smoother skin. Unsaturated fatty acids, however, undergo a chemical change known as auto-oxidation, wherein the double bonds of an unsaturated fatty acid can undergo cleavage in the presence of oxygen and free radicals, releasing volatile aldehydes and ketones. Such auto-oxidation can often result in rancidity of the substance, which is associated with an unpleasant odor and color. Accordingly, formulators have utilized antioxidant cocktails and nitrogen packaging processes to decrease peroxidation of unsaturated fatty acids.

Inhibition of oxidation of polyunsaturated lipids has been addressed in the art. For example, U.S. Pat. No. 6,428,461 discloses mixing polyunsaturated lipids with a combination of polyamines such as spermidine, putrescine, or mixtures thereof, in food processing applications. The prior art falls short, however, of disclosing optimal antioxidants for unsaturated fatty acids in personal care compositions.

Consequently, there is a continuing need to develop new methods of inhibiting oxidation of unsaturated fatty acids in personal care compositions.

STATEMENT OF INVENTION

One aspect of the invention provides a personal care composition comprising:
(a) an antioxidant compound of Formula I:

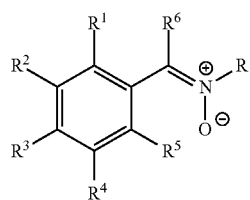

wherein R is $C_1$-$C_{10}$ alkyl, $C_3$-$C_{12}$ cycloalkyl, aryl, or aryl-alkyl; $R^1$, $R^2$, $R^3$, $R^4$, and $R^5$ are independently H, $C_1$-$C_{10}$ alkyl, hydroxy, $C_1$-$C_6$ alkoxy, —COOH, —COO$^-$M$^+$, or —O$^-$M$^+$, where M$^+$ is sodium or potassium or ammonium ion, provided that at least one of $R^1$, $R^2$, $R^3$, $R^4$, and $R^5$ is hydroxy; and $R^6$ is H, $C_1$-$C_{10}$ alkyl, $C_3$-$C_{12}$ cycloalkyl or phenyl;
(b) an unsaturated fat; and
(c) a dermatologically acceptable carrier.

DETAILED DESCRIPTION

Figure 1:
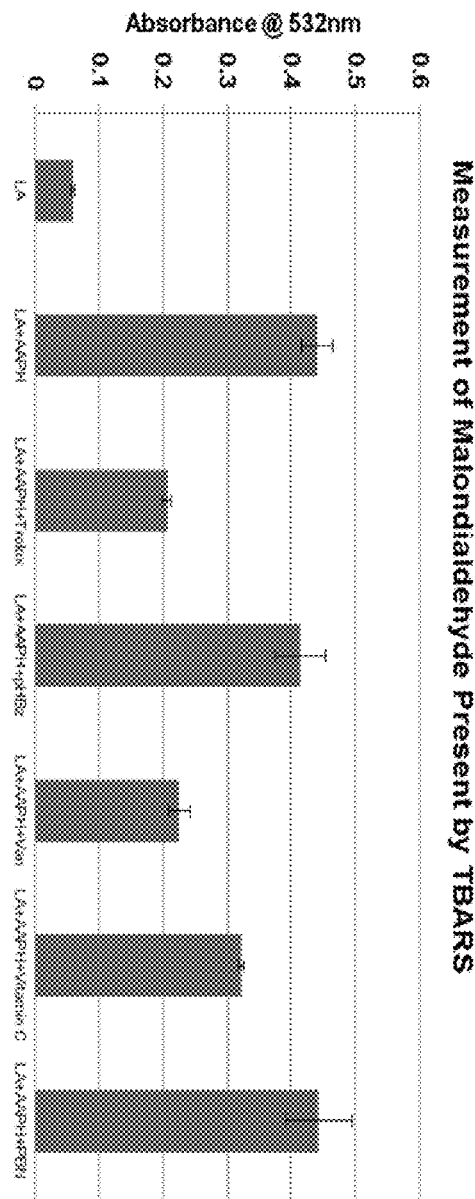
FIG. 1 shows the presence of unsaturated fatty acid peroxidation product MDA as indicated by UV absorbance at 532 nm of linolenic acid control, linolenic acid with AAPH, and linolenic acid with AAPH in the presence of comparative and inventive antioxidants.

The inventors have now surprisingly found that nitrone compounds of Formula I, which contain nitrone and phenolic functionalities as part of the structure, provide equivalent efficacy as inhibitors of oxidation of unsaturated fats at lower concentration, or higher efficacy at equivalent concentrations, as compared to convention antioxidants. It has also been found that the performance of nitrones cannot be achieved by simply adding two different antioxidants, e.g., one with a phenolic functionality and another with nitrone functionality. Rather, the presence of both functionalities in the same molecule is an important aspect of their favorable performance.

In the present invention, "personal care" is intended to refer to cosmetic and skin care compositions (i.e., for application to the skin, including, for example, body washes and cleansers, as well as leave on application to the skin, such as lotions, creams, gels, gel creams, shaving gel, shaving cream, shaving foam, serums, toners, wipes, liquid foundations, make-ups, tinted moisturizer, oils, face/body sprays, topical medicines, and sunscreens), hair care compositions (e.g., shampoos, rinse-off and leave-on conditioners, styling gels, hairsprays, mousses, and hair coloring products), and oral care compositions (e.g., toothpaste, mouthwash, and chewing gum). Preferably, the personal care compositions are cosmetically acceptable. "Personal care" relates to compositions to be topically administered (i.e., not ingested). Preferably, the personal care composition is cosmetically acceptable. "Cosmetically acceptable" refers to ingredients typically used in personal care compositions, and is intended to underscore that materials that are toxic when present in the amounts typically found in personal care compositions are not contemplated as part of the present invention. The compositions of the invention may be manufactured by processes well known in the art, for example, by means of conventional mixing, dissolving, granulating, emulsifying, encapsulating, entrapping or lyophilizing processes.

Unless otherwise indicated, numeric ranges, for instance as in "from 2 to 10," are inclusive of the numbers defining the range (e.g., 2 and 10). Unless otherwise indicated, ratios, percentages, parts, and the like are by weight. "Room temperature," as used in this specification, is the ambient temperature, for example, 20-25° C.

"Alkyl," as used in this specification, encompasses straight and branched chain aliphatic hydrocarbon groups having the indicated number of carbon atoms. If no number is indicated, then 1-6 alkyl carbons are contemplated. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), $C_2$-$C_6$ alkene, cyano, amido, and/or ester. Unless otherwise indicated, the foregoing substituent groups are not themselves further substituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), $C_2$-$C_6$ alkene, cyano, amido, and/or ester. A preferred substituent is $C_1$-$C_6$ alkyl. Unless otherwise indicated, the foregoing substituent groups are not themselves further substituted.

An "aryl" group is a $C_6$-$C_{19}$ aromatic moiety comprising one to three aromatic rings. Preferably, the aryl group is a $C_6$-$C_{10}$ aryl group. Preferred aryl include, without limitation, phenyl, naphthyl, anthracenyl, and fluorenyl. More preferred are phenyl and naphthyl. Unless otherwise indicated, the aryl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), $C_2$-$C_6$ alkene, cyano, amido, and/or ester. Unless otherwise indicated, the foregoing substituent groups are not themselves further substituted.

Generally, the present invention provides compositions useful for processing unsaturated fatty acids in personal care compositions by their direct physical admixture with a compound of Formula I in amounts effective such that the resulting treated unsaturated fatty acid experiences an increase in oxidative stability, which exceeds that possible by blending the same unsaturated fatty acid with other conventional antioxidants.

Accordingly, as noted above, in one aspect the invention provides compositions useful for inhibiting oxidation of unsaturated fats comprising an effective amount of an antioxidant compound of Formula I. In some embodiments, R in the compounds of Formula I is $C_1$-$C_8$ alkyl, alternatively $C_1$-$C_6$ alkyl, or alternatively $C_1$-$C_4$ alkyl. In some embodiments, R is t-butyl, i-propyl, n-propyl, ethyl, or methyl. In some embodiments, R is 2,4,4-trimethylpentyl. In some embodiments, R in the compounds of Formula I is $C_3$-$C_{12}$ cycloalkyl, alternatively $C_4$-$C_7$ cycloalkyl. In some embodiments, R is cyclohexyl. In some embodiments, R is aryl, preferably phenyl. In some embodiments, R is aryl-alkyl, preferably benzyl. In some embodiments, $R^1$ is H, OH, or $O^-M^+$. In some embodiments, $R^4$ is H or $C_1$-$C_{10}$ alkyl (e.g., methyl). In some embodiments, $R^5$ is H. In some embodiments, $R^1$, $R^4$, and $R^5$ are simultaneously H. In some embodiments, $R^3$ is OH. In some embodiments, $R^2$ is H, $C_1$-$C_{10}$ alkyl, hydroxy, $C_1$-$C_6$ alkoxy, —COOH, or —COO$^-$M$^+$, where M$^+$ is sodium.

In some embodiments of the composition of the invention, the compound of Formula I is as shown in Table 1:

TABLE 1

Specified Compounds of Formula I (VAN-tBHA)

(Z)-N-(4-hydroxy-3-methoxybenzylidene)-2-methylpropan-2-amine oxide (DMHBz-CyHHA)

(Z)-N-(4-hydroxy-3,5-dimethylbenzylidene)cyclohexanamine oxide (VAN-IPHA)

(Z)-N-(4-hydroxy-3-methoxybenzylidene)propan-2-amine oxide (VAN-iOHA)

(Z)-N-(4-hydroxy-3-methoxybenzylidene)-2,4,4-trimethylpentan-2-amine oxide (VAN-CyHHA)

(Z)-N-(4-hydroxy-3-methoxybenzylidene)cyclohexanamine oxide

TABLE 1-continued

Specified Compounds of Formula I (pHBz-EHA)

(Z)-N-(4-hydroxybenzylidene)ethanamine oxide (pHBz-PHA)

(Z)-N-(4-hydroxybenzylidene)propan-1-amine oxide (pHBz-IPHA)

(Z)-N-(4-hydroxybenzylidene)propan-2-amine oxide (pHBz-tBHA)

(Z)-N-(4-hydroxybenzylidene)-2-methylpropan-2-amine oxide (SAL-IPHA)

(Z)-N-(2-hydroxybenzylidene)propan-2-amine oxide (FSANa-IPHA)

sodium (Z)-2-hydroxy-5-((isopropyloxidoimino)methyl)benzoate (DHBz-IPHA)

(Z)-N-(2,4-dihydroxybenzylidene)propan-2-amine oxide

TABLE 1-continued

Specified Compounds of Formula I (DHBzNa-IPHA)

sodium (Z)-N-(4-hydroxy-2-oxidobenzylidene)propan-2-amine oxide (DMHBz-IPHA)

(Z)-N-(4-hydroxy-3,5-dimethylbenzylidene)propan-2-amine oxide (DMHBz-tBHA)

(Z)-N-(4-hydroxy-3,5-dimethylbenzylidene)-2-methylpropan-2-amine oxide (DMHBz-iOHA)

(Z)-N-(4-hydroxy-3,5-dimethylbenzylidene)-2,4,4-trimethylpentan-2-amine oxide (SAL-tBHA)

(Z)-N-(2-hydroxybenzylidene)-2-methylpropan-2-amine oxide (SAL-CyHHA)

(Z)-N-(2-hydroxybenzylidene)cyclohexanamine oxide

TABLE 1-continued

Specified Compounds of Formula I

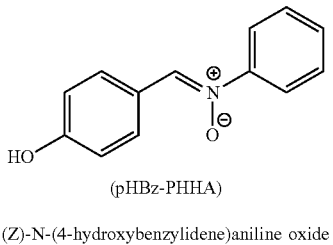

(pHBz-PHHA)

(Z)-N-(4-hydroxybenzylidene)aniline oxide

Unsaturated fats, for purposes of the present invention, are fatty oils or fatty acids (i.e., carboxylic acids) with a long chain aliphatic tail having one or more double bonds between carbon atoms. In certain embodiments, the unsaturated fats contain 10 to 30 carbon atoms, preferably 12 to 24 carbon atoms, and more preferably 16 to 22 carbon atoms. The unsaturated fats can be straight, branched, or ring structures. In certain embodiments, the fatty chains are straight hydrocarbon chains having cis configurations at the carbon-carbon double bonds along the main chains. Suitable unsaturated fats for use in this invention can be obtained from natural sources or can be prepared synthetically. Natural sources of suitable unsaturated fats include, for example, vegetable, animal, and marine oils containing long chain unsaturated fatty acids, including, but not limited to, flaxseed oil, corn oil, sunflower oil, cottonseed oil, canola oil, soybean oil, tung oil, lard, cod liver oil, capelin oil, menhaden oil, and so forth. In certain embodiments, the unsaturated fatty acid is an essential fatty acid having one or more double bonds either three, six, or nine carbons removed from the methyl end, i.e., omega-3, omega-6, and omega-9 fatty acids, respectively. In certain preferred embodiments, the unsaturated fatty acid to be treated according to the inventive method is selected from the group consisting of linolenic acid, linoleic acid, and combinations of these.

A person of ordinary skill in the art can readily determine the effective amount of the antioxidant compound of Formula I that should be used in a particular composition in order to provide the benefits described herein (e.g., inhibition of oxidation of unsaturated fats), via a combination of general knowledge of the applicable field as well as routine experimentation where needed. By way of non-limiting example, the unsaturated fats are blended with compositions containing compounds of Formula I in a range of from 0.01 to 1 weight %, preferably of from 0.03 to 0.5 weight %, and more preferably from 0.5 to 0.1 weight %, based on the total weight of the composition. In certain embodiments, the unsaturated fats are blended with the compounds of Formula I in a weight ratio between 98:0.1 to 5:1, preferably between 48:0.1 to 7:1, and more preferably between 20:1 to 10:1.

Compounds of Formula I may be readily prepared by those skilled in the art using known synthetic techniques, as disclosed in PCT Published Application No. WO 2013/081778. For instance, the compounds may be prepared by the reaction of a phenyl aldehyde compound (containing one or more hydroxyl groups on the phenyl, such as 4-hydroxybenzaldehyde) with an alkylhydroxylamine compound, followed by isolation and purification of the desired product.

Compositions of the invention can also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, emulsions, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The dermatologically acceptable carrier of the invention may also include, for instance, water, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment, glycerin, a mineral oil, silicon feel modifiers, preservatives, emollients, or mixtures thereof.

Other additives may be included in the compositions of the invention such as, but not limited to, abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), other antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins (e.g., Vitamin C) and derivatives thereof.

The compositions of the invention may be, for example, in the form of an oil, a gel, a solid stick, a lotion, a cream, a milk, an aerosol, a spray, a foam, a mousse, an ointment or a fatty ointment or a powder. Compositions of the invention may be used in a variety of personal care applications, such as in cosmetics and in skin care (e.g., lotions, creams, oils, topical medicines, and sunscreens). The compositions of the invention may be manufactured by processes well known in the art, e.g., by means of conventional mixing, dissolving, granulating, emulsifying, encapsulating, entrapping or lyophilizing processes.

Although the compositions of the present invention are suitable for personal care products in particular, they are not necessarily limited thereto. They could also be used in other applications involving unsaturated fatty acids including, for example, medicinal ointments, lotions, and creams, and food and beverage products, or other materials susceptible to oxidation.

As noted above, compounds of Formula I are highly effective as radical scavengers. They exhibit significantly better antioxidant attributes compared to previously known antioxidants for inhibition of oxidation of unsaturated fats, and can also stabilize hydroxyl radicals that are generated from highly oxidative molecules (e.g., those generated from glycolic acid or vitamin C). Advantageously, it is believed that the presence of the nitrone and phenolic functionalities allows a regenerative mechanism to take place. Furthermore it has been found that the performance of nitrones that have a phenolic group cannot be achieved by simply adding two different antioxidants, one with a phenolic functionality and another with nitrone functionality. Rather, the presence of both functionalities in the same molecule is an important aspect of their favorable performance.

Some embodiments of the invention will now be described in detail in the following Examples.

EXAMPLES

Example 1

Efficacy of Stabilizing Unsaturated Fatty Acids in Formulation—TBARS Assay

Lipids are a group of natural molecules including fats, waxes, sterols, vitamins and glycerides. The biological functions of lipids are storing energy, signaling and acting as cell membranes structural components. The common damage to lipids is peroxidation. The oxidation occurs on lipids through a chain reaction mechanism. Unsaturated lipids or fatty acids are vulnerable to free radical attack, resulting in cell damage. Linoleic acid and linolenic acid are two indispensable fatty acids for humans and animals. To investigate the efficacy of inventive compounds on preventing fatty acid peroxidation, linolenic acid was chosen as the subject. The efficacy of Van-IPHA and pHBz-IPHA were compared with other common antioxidants, such as Trolox, phenyl-alpha-tert-butyl nitrone (PBN), vitamin C, and vitamin E.

Malondialdehyde (MDA) is a naturally occurring product of unsaturated fatty acid peroxidation, and the Thiobarbituric Acid (TBA) Reactive Substances (TBARS) assay is a well-established method to evaluate peroxidation by monitoring the production of MDA. The signal of MDA-TBA adducts increases when MDA increases in the sample. Inventive and comparative samples treated with AAPH contain the components recited in Table 2.

TABLE 2

| | Samples Treated with AAPH | | | | | | |
|---|---|---|---|---|---|---|---|
| Sample | Linoleic Acid (mM) | Trolox (mM) | pHBz-IPHA (mM) | Van-IPHA (mM) | Vitamin C (mM) | PBN (mM) | AAPH (mM) |
| LA (control) | 2 | — | — | — | — | — | — |
| LA + AAPH* | 2 | — | — | — | — | — | 2 |
| LA + AAPH + Trolox* | 2 | 0.2 | — | — | — | — | 2 |
| LA + AAPH + pHBz | 2 | — | 0.2 | — | — | — | 2 |
| LA + AAPH + Van-IPHA | 2 | — | — | 0.2 | — | — | 2 |
| LA + AAPH + Vitamin C* | 2 | — | — | — | 0.2 | — | 2 |

TABLE 2-continued

| | Samples Treated with AAPH | | | | | | |
|---|---|---|---|---|---|---|---|
| Sample | Linoleic Acid (mM) | Trolox (mM) | pHBz-IPHA (mM) | Van-IPHA (mM) | Vitamin C (mM) | PBN (mM) | AAPH (mM) |
| LA + AAPH + PBN* | 2 | — | — | — | — | 0.2 | 2 |

LA (linolenic acid) is available from Sigma-Aldrich
AAPH (2,2'-Azobis(2-methylpropionamidine) dihydrochloride) is available from Sigma-Aldrich
Trolox (6-hydroxy-2,5,7,8-tetramethylchroman-2-carboxylic acid) is available from Sigma-Aldrich
Vitamin C is available from Fisher Scientific
PBN (phenyl-alpha-tert-butyl nitrone) is available from Fisher Scientific
*Comparative The UV absorbance of each sample at 532 nm was measured to determine the concentration of MDA in the sample after treatment with AAPH for 24 hours at 37° C. Samples were loaded into 96-well plate, and SpectraMax Plus 384 UV-Vis Reader was used to take the measurement at room temperature. FIG. 1 shows that the UV signal increases from about 0.05 to above 0.4 upon adding AAPH into the linolenic acid solution. The samples with Trolox and Van-IPHA have a signal increase of approximately 0.2, which is half of the signal of the positive control. Vitamin C also shows protection with a signal increase to about 0.3, while PBN does not demonstrate a significant protection in this test. Accordingly, the TBARS assay indicates that Van-IPHA shows increased protection of fatty acids against peroxidation by AAPH.

Efficacy of Stabilizing Unsaturated Fatty Acids in Formulation—LC-UV/MS

Figure 2:
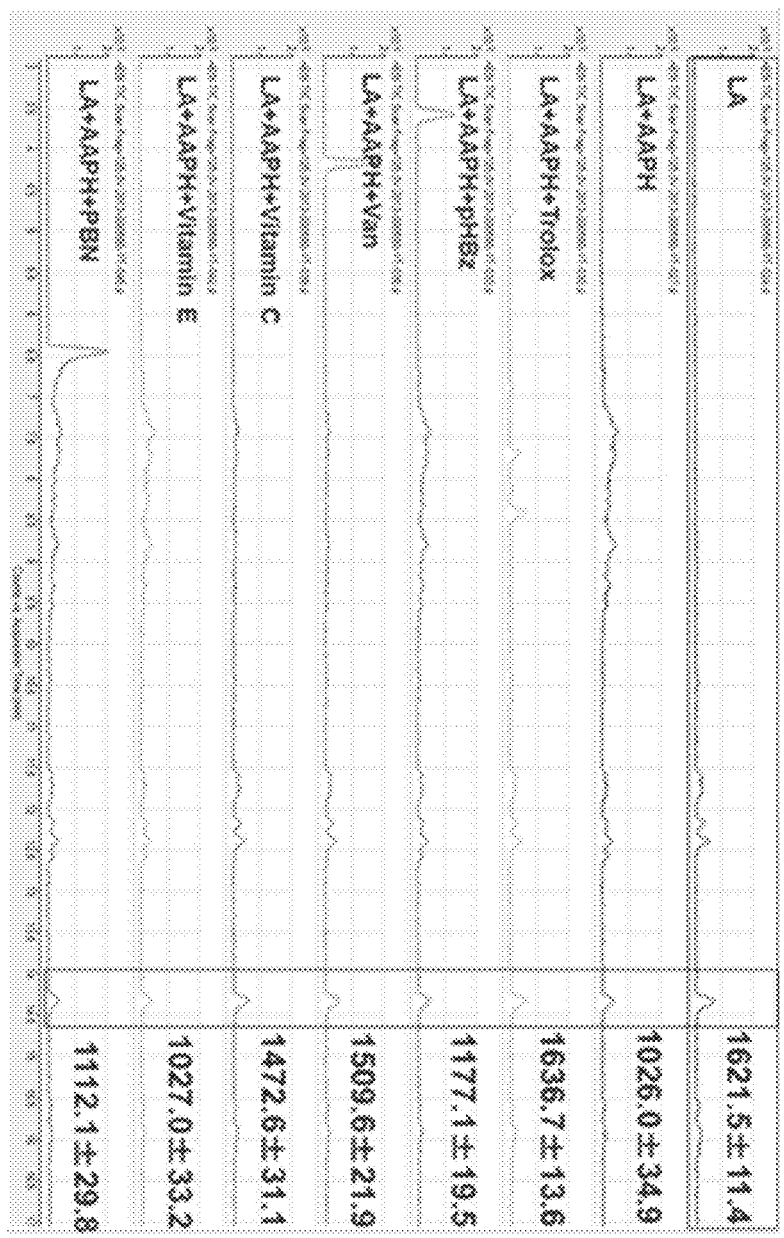
FIG. 2 shows the liquid chromatography chromatograms of linolenic acid control, linolenic acid with AAPH, and linolenic acid with AAPH in the presence of comparative and inventive antioxidants.

The TBARS assay is considered an indirect method of measuring the fatty acids peroxidation, as it measures one oxidative product (MDA), without examining the fatty acid itself. A LC-UV/MS method was thus developed to measure the levels of fatty acids and all potential oxidative products in the sample, wherein the LC chromatograms of various samples was taken after treating each sample with AAPH for 24 hours at 37° C. Agilent 6538 quadrupole-time of flight mass spectrometry system via a dual spray ESI interface coupled with an Agilent 1290SL binary gradient liquid chromatograph system was used. The column of 150×3 mm ID 2.5 μm Waters CSH Xselect C18 was kept at 50° C. Mobile phase A consisted of 0.1 v % formic acid in water and B consisted of 0.1 v % formic acid in isopropanol. The gradient increased from 5% B to 100% B in 20 minutes, and the flow rate was 0.6 mL/min. Agilent DAD was used for UV detection. FIG. 2 shows the LC chromatograms of the various samples, the peak eluting at 14.4 minutes is linolenic acid, and the number next to the peak in FIG. 2 is the average peak area (UV at 214 nm) of three replicates with standard deviation. With AAPH initiated peroxidation, the peak area of linolenic acid drops from 1621 to 1026, indicating that the degradation occurred; while new peaks emerge at 7-10 minutes, representing the derivative products from linolenic acid. In the samples containing Trolox or Van-IPHA, almost no change was observed for Trolox and only a slight drop was observed for Van-IPHA in terms of the peak area of linolenic acid. Vitamin C was observed to be the next best anti-oxidant; however, the instability of vitamin C is its downside. Vitamin E doesn't perform well probably due to its incompatibility with the testing solvent system. PBN showed almost no protection to linolenic acid. The observations from direct analysis of linoleic acid are consistent with the TBARS assay results. Both methods demonstrated that Van-IPHA is an advantageously effective alternative for preventing unsaturated fatty acid oxidation.

Example 2

Efficacy of Stabilizing Unsaturated Fatty Acids in Formulation

The efficacy of stabilizing the unsaturated fatty acids in skin care formulations with inventive antioxidants was investigated. Linoleic acid chosen as the protecting target. Aqueous solutions of inventive and comparative samples evaluated for stability contain the components recited in Table 3.

TABLE 3

Aqueous Formulations Evaluated for Oxidative Stability

| Sample | Xanthan Gum (wt %) | Glycerin (wt %) | Linoleic Acid (wt %) | Van-IPHA (wt %) | pHBz-IPHA (wt %) | Trolox (wt %) |
|---|---|---|---|---|---|---|
| LA (control) | 2 | 2 | 0.1 | — | — | — |
| Van-IPHA | 2 | 2 | 0.1 | 0.02 | — | — |
| pHBz-IPHA | 2 | 2 | 0.1 | — | 0.02 | — |
| Trolox* | 2 | 2 | 0.1 | — | — | 0.02 |

Figure 3:
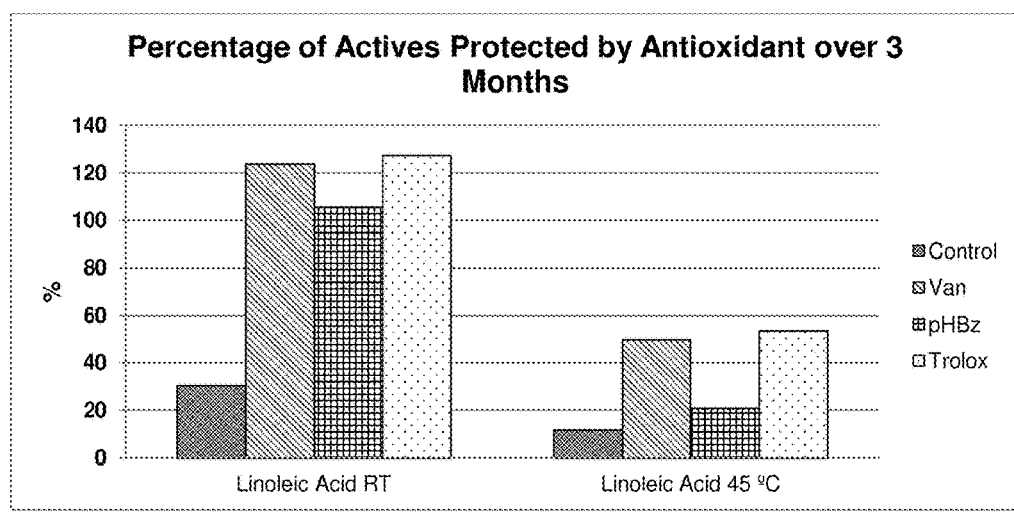
FIG. 3 shows the percentage of actives protected at both room temperature and 45° C. over a period of 3 months in the presence of comparative and inventive antioxidants.

Xanthan Gum is available from CP Kelco
Glycerin is available from is available from Spectrum Chemical
Retinol is available from Spectrum Chemical
Trolox is available from Sigma-Aldrich
*Comparative Each aqueous formulation in Table 3 above was prepared in a 50 mL jar. Samples were kept at room temperature and 45° C. for three months. A LC-UV method was developed to monitor the levels of Van-IPHA/pHBz-IPHA/Trolox and a LC-MS SIM method was used to monitor the level of linoleic acid in the formulations. An Agilent 6410 triple quadrupole mass spectrometry system via a dual spray ESI interface coupled to an Agilent 1260 Infinity liquid chromatograph system was used. A Waters CSH Xselect C18 150×3 mm ID 2.5 Lm column was kept at 70° C. Mobile phase A consisted of 0.1 v % formic acid in water and B consisted of 0.1 v % formic acid in isopropanol. The gradient increased from 5% B to 100% B in 25 minutes, and the flow rate was 0.6 mL/min. Agilent DAD at 300 nm was used for UV detection of the antioxidants: Van-IPHA; pHBz-IPHA; and Trolox. Linoleic acid was detected by SIM LC-MS in negative ionization mode at m/z 279.2. The analyses were taken place at Day 0, 7, 33, 48, 74 and 89 days. The final results were shown at FIG. 3. For the protection of linoleic acid, there was almost no degradation in the presence of Van-IPHA, pHBz-IPHA, and Trolox, comparing to only one third left in the control sample (no antioxidant) after three months storage. The accelerated test at 45° C. was used to predict the shelf life of two years at room temperature. For the samples at 45° C., the levels of linoleic acid with Van-IPHA, pHBz-IPHA, and Trolox were higher than that in control (no antioxidant). Both inventive Van-IPHA and pHBz-IPHA demonstrate stabilization of unsaturated fatty acids and prolonged shelf life of relevant skincare products as compared with convention antioxidants.

Example 3

Efficacy of Stabilization of Unsaturated Fatty Acids in Formulations Containing Oils Many body wash or body lotion products use sunflower seed oil (SSO) as ingredient, which contains unsaturated fatty acids. Hexanal is one of the major oxidative products generated from those products, and the strong smell is very unpleasant and not favored by customers. Formulators of such products use the smell of hexanal as the major criteria to check the acceptance of certain products after storage at various temperatures over time. Antioxidants are in need in the formulation to prevent or slow down the oxidation/degradation of oils in order to lower the generation of hexanal under noticeable threshold. Van-IPHA and pHBz-IPHA were investigated for the efficacy of stabilizing of unsaturated fatty acids containing oil in formulation.

Stabilization of Unsaturated Fatty Acids by pHBz-IPHA and Van-IPHA in Formulations Containing SSO Exemplary and comparative compositions containing SSO, and pHBz-IPHA or Van-IPHA, include the components recited in Table 4.

TABLE 4

Exemplary and Comparative Sunflower Seed Oil Compositions

| Component | Sample | | | | | | | |
|---|---|---|---|---|---|---|---|---|
| | 3% Oil + Nitrone | 3% Oil Control | 5% Oil + Nitrone | 5% Oil Control | 10% Oil + Nitrone | 10% Oil Control | 95% Oil + Nitrone | 95% Oil Control |
| Water (wt %) | 91.9 | 92 | 89.9 | 90 | 84.9 | 85 | 0.9 | 1 |
| Xanthan Gum (wt %) | 2 | 2 | 2 | 2 | 2 | 2 | 0 | 0 |
| Glycerin (wt %) | 2 | 2 | 2 | 2 | 2 | 2 | 3 | 3 |
| Tween 20 (wt %) | 1 | 1 | 1 | 1 | 1 | 1 | 1 | 1 |
| Nitrone (wt %) (pHBz-IPHA or Van-IPHA) | 0.1 | 0 | 0.1 | 0 | 0.1 | 0 | 0.1 | 0 |
| SSO (wt %) | 3 | 3 | 5 | 5 | 10 | 10 | 95 | 95 |

Xanthan Gum is available from CP Kelco
Glycerin is available from is available from Spectrum Chemical
Tween 20 is available from Sigma-Aldrich
SSO (Sunflower Seed Oil) is available from Sigma-Aldrich A headspace GC-MS method was developed in house to monitor the hexanal production at day 0, two weeks, one month, two months and three months after the initial day. Samples of each formulation were placed into headspace vials and heated for 5 minutes at 80° C. 1 mL of the headspace from each sample was injected into the GC using a Gerstel MultiPurpose Sampler with a heated gas tight needle heated to 85° C. Separation was performed on an Agilent 30 m×250 μm×0.25 μm column. Detection of hexanal was performed in the MS with SIM for m/z 56, m/z 72 and m/z 82.

Figure 4:
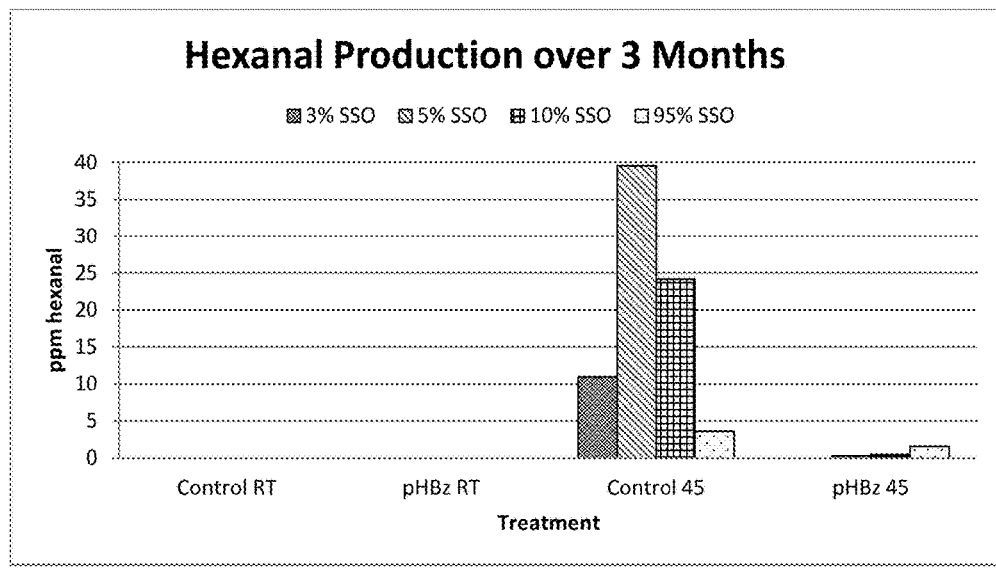
FIG. 4 shows the hexanal production from formulations containing 3 wt %, 5 wt %, 10 wt %, and 95 wt % Sunflower Oil with and without pHBz-IPHA after three months of incubation at both room temperature (RT) and 45° C.

The final results of hexanal production from formulations containing 3 wt %, 5 wt %, 10 wt %, and 95 wt % SSO with and without pHBz-IPHA are shown in FIG. 4. At room temperature, the degradation or oxidation was slow and no hexanal was detectable after 3 months in all samples. In the accelerated test at 45° C., various amounts (10-40 ppm) of hexanal were produced in the formulation containing 3 wt %, 5 wt %, or 10 wt % SSO after three months. In comparison, in the samples containing 0.1 wt % pHBz, the production of hexanal was much less. Due to the large composition difference of 95 wt % SSO, the improvement was not as pronounced as the others. The results demonstrate that pHBz-IPHA is an advantageously effective alternative to stabilize SSO to reduce the hexanal production in personal care products.

Figure 5:
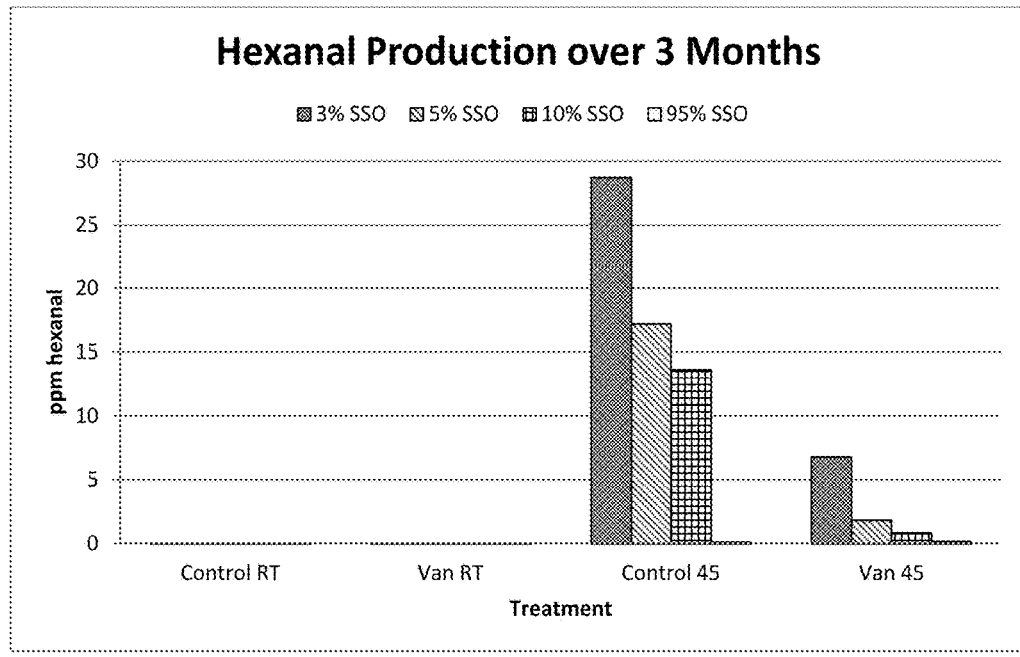
FIG. 5 shows the hexanal production from formulations containing 3 wt %, 5 wt %, 10 wt %, and 95 wt % Sunflower Oil with and without Van-IPHA after three months of incubation at both room temperature (RT) and 45° C.

The final results of hexanal production from the formulations contain 3 wt %, 5 wt %, 10 wt %, and 95 wt % SSO with and without Van-IPHA are shown in FIG. 5. In the formulations containing Van-IPHA, similar results were observed as the effect of pHBz-IPHA reported above. The results demonstrate that Van-IPHA is an advantageously effective alternative to stabilize SSO to reduce the hexanal production in personal care products.

Stabilization of Unsaturated Fatty Acids by pHBz-IPHA and Van-IPHA in Formulations Containing SBO Formulations were also made using soybean oil (SBO) as the concentration of polyunsaturated fatty acids in SBO is higher and the desire to use SBO in the skin care market is prominent for its lower cost. Exemplary and comparative compositions containing SBO, and pHBz-IPHA or Van-IPHA, include the components recited in Table 5.

Figure 6:
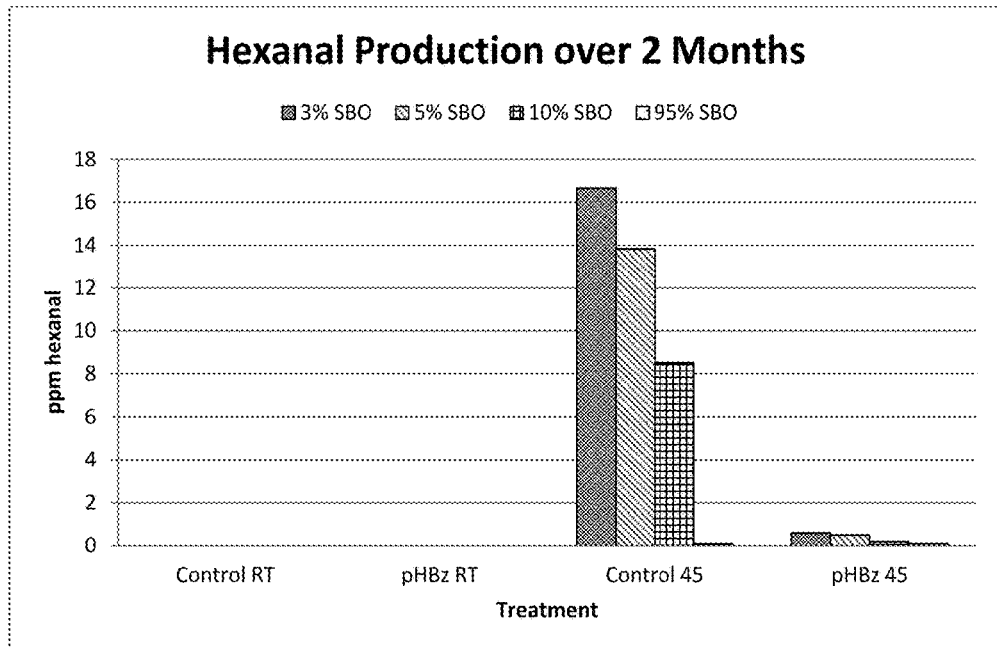
FIG. 6 shows the hexanal production from formulations containing 3 wt %, 5 wt %, 10 wt %, and 95 wt % Soybean Oil with and without pHBz-IPHA after two months of incubation at both room temperature (RT) and 45° C.
Figure 7:
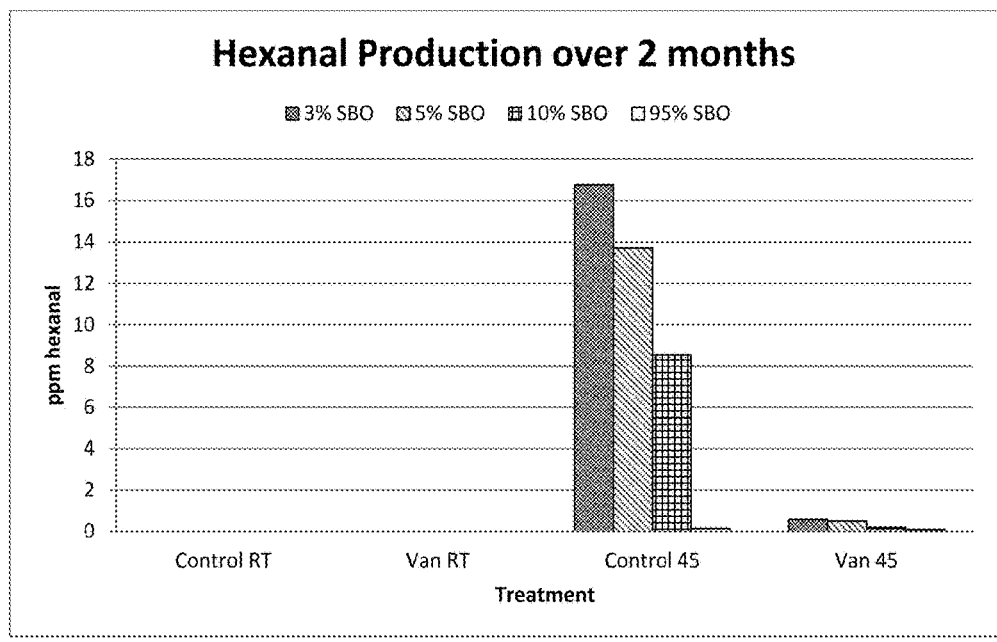
FIG. 7 shows the hexanal production from formulations containing 3 wt %, 5 wt %, 10 wt %, and 95 wt % Soybean Oil with and without Van-IPHA after two months of incubation at both room temperature (RT) and 45° C.

FIG. 6 and FIG. 7 show the results of hexanal production from SBO formulations containing pHBz-IPHA or Van-IPHA at room temperature and 45° C. after 2 months. As with the SSO formulations, very little hexanal was produced at room temperature and there is a large decrease in the hexanal produced in the formulations, 3 wt %, 5 wt %, and 10 wt % SBO, held at 45° C. These data along with the SSO data suggest pHBz-IPHA and Van-IPHA have the ability to protect polyunsaturated fatty acid containing triglycerides against oxidation.

What is claimed is:

1. A personal care composition comprising:
   (a) an antioxidant compound selected from the group consisting of (Z)—N-(4-hydroxy-3-methoxybenzylidene)propan-2-amine, (Z)—N-(4-hydroxybenzylidene)propan-2-amine oxide, and combinations thereof;
   (b) an unsaturated fat, wherein the unsaturated fat is at least one of linoleic acid and or linolenic acid; and
   (c) a dermatologically acceptable carrier.

2. The composition of claim 1, wherein the unsaturated fat and antioxidant compounds are present in a ratio of from 98:0.1 to 5:1.

3. The composition of claim 1, wherein the unsaturated fat and antioxidant compounds are present in a ratio of from 48:0.1 to 7:1.

4. The composition of claim 1, wherein the unsaturated fat and antioxidant compounds are present in a ratio of from 20:1 to 10:1.

* * * * *

TABLE 5

Exemplary and Comparative Sunflower Seed Oil Compositions

| Component | Sample | | | | | | | |
|---|---|---|---|---|---|---|---|---|
| | 3% Oil + Nitrone | 3% Oil Control | 5% Oil + Nitrone | 5% Oil Control | 10% Oil + Nitrone | 10% Oil Control | 95% Oil + Nitrone | 95% Oil Control |
| Water (wt %) | 91.9 | 92 | 89.9 | 90 | 84.9 | 85 | 0.9 | 1 |
| Xanthan Gum (wt %) | 2 | 2 | 2 | 2 | 2 | 2 | 0 | 0 |
| Glycerin (wt %) | 2 | 2 | 2 | 2 | 2 | 2 | 3 | 3 |
| Tween 20 (wt %) | 1 | 1 | 1 | 1 | 1 | 1 | 1 | 1 |
| Nitrone (wt %) (pHBz-IPHA or Van-IPHA) | 0.1 | 0 | 0.1 | 0 | 0.1 | 0 | 0.1 | 0 |
| SBO (wt %) | 3 | 3 | 5 | 5 | 10 | 10 | 95 | 95 |

Xanthan Gum is available from CP Kelco
Glycerin is available from is available from Spectrum Chemical
Tween 20 is available from Sigma-Aldrich
SBO (Soybean Oil) is available from Fisher Scientific